(12) United States Patent
Khandaker et al.

(10) Patent No.: US 10,064,736 B2
(45) Date of Patent: Sep. 4, 2018

(54) ENGINEERED INTERVERTEBRAL DISC (IVD) FOR DEGENERATED DISC DISEASE

(71) Applicant: UNIVERSITY OF CENTRAL OKLAHOMA, Edmond, OK (US)

(72) Inventors: Morshed Khandaker, Edmond, OK (US); Shahram Riahinezhad, Edmond, OK (US)

(73) Assignee: University of Central Oklahoma, Edmond, OK (US)

( * ) Notice: Subject to any disclaimer, the term of this patent is extended or adjusted under 35 U.S.C. 154(b) by 101 days.

(21) Appl. No.: 15/188,654

(22) Filed: Jun. 21, 2016

(65) Prior Publication Data

US 2016/0374820 A1 Dec. 29, 2016

Related U.S. Application Data

(60) Provisional application No. 62/279,136, filed on Jan. 15, 2016, provisional application No. 62/184,298, filed on Jun. 25, 2015.

(51) Int. Cl.
*A61F 2/44* (2006.01)
*A61L 27/52* (2006.01)
(Continued)

(52) U.S. Cl.
CPC .............. *A61F 2/441* (2013.01); *A61L 27/18* (2013.01); *A61L 27/34* (2013.01);
(Continued)

(58) Field of Classification Search
CPC .................................. A61F 2/44; A61F 2/441
(Continued)

(56) References Cited

U.S. PATENT DOCUMENTS 5,047,055 A 9/1991 Bao et al.
5,674,295 A 10/1997 Ray et al.
(Continued)

FOREIGN PATENT DOCUMENTS

WO WO2016028618 2/2016

OTHER PUBLICATIONS

International Search Report dated Sep. 7, 2016 from correponding International Appl. No. PCT/US16/38910 filed Jun. 23, 2016.
(Continued)

*Primary Examiner* — Si Ming Ku
(74) *Attorney, Agent, or Firm* — Berenato & White, LLC

(57) ABSTRACT

The present invention provides a process by which both non-tissue engineered and tissue engineered cartilaginous-like structures can be fabricated. The process of the present invention provides a method to produce electrospun nanofiber-anchored NP gels. The present invention provides a functional design for novel engineered IVD. The present invention provides a method for fabrication of both non-tissue and tissue engineered IVDs. These cartilaginous-like structures can be used to produce replacements for degenerated natural IVD. The method of the present invention uses electrospun PCL nanofiber mesh to anchor the NP. The method of the present invention can create angle-ply AF structure around the circumference of NP to mimic the architecture of native IVD. The method of the present invention anchors the top and bottom sides of NP by using non-woven aligned or random nanofiber mesh to create scaffold for the generation of endplate (EP) tissue.

16 Claims, 13 Drawing Sheets

(51) Int. Cl.
*A61L 27/18* (2006.01)
*A61L 27/38* (2006.01)
*A61L 27/34* (2006.01)
*A61L 27/26* (2006.01)

(52) U.S. Cl.
CPC ....... *A61L 27/3817* (2013.01); *A61L 27/3856* (2013.01); *A61L 27/52* (2013.01); *A61F 2002/4495* (2013.01); *A61L 27/26* (2013.01); *A61L 2400/12* (2013.01); *A61L 2430/38* (2013.01)

(58) Field of Classification Search
USPC ............................................ 623/17.11–17.16
See application file for complete search history.

(56) References Cited

U.S. PATENT DOCUMENTS

| | | | |
|---|---|---|---|
| 6,733,533 | B1 | 5/2004 | Lozier |
| 6,746,485 | B1 | 6/2004 | Zucherman et al. |
| 6,902,932 | B2 | 6/2005 | Altman et al. |
| 6,997,956 | B2 | 2/2006 | Cauthen |
| 8,696,750 | B2 | 4/2014 | Santerre et al. |
| 9,044,335 | B2 | 6/2015 | Bonassar et al. |
| 9,078,731 | B2 | 7/2015 | Mortarino |
| 9,198,768 | B1* | 12/2015 | Pisharodi ............... A61F 2/447 |
| 9,295,560 | B2 | 3/2016 | Carpenter |
| 9,359,694 | B2 | 6/2016 | Khandaker et al. |
| 2002/0029083 | A1* | 3/2002 | Zucherman ............... A61F 2/12 623/17.16 |
| 2005/0090901 | A1* | 4/2005 | Studer ................... A61F 2/441 623/17.12 |
| 2006/0160214 | A1 | 7/2006 | Masuda et al. |
| 2009/0076610 | A1* | 3/2009 | Afzal .................... A61F 2/442 623/17.16 |
| 2009/0171467 | A1 | 7/2009 | Mann et al. |
| 2010/0179659 | A1* | 7/2010 | Li ......................... A61F 2/441 623/17.16 |
| 2010/0191335 | A1 | 7/2010 | Root et al. |
| 2011/0098826 | A1 | 4/2011 | Mauck et al. |
| 2012/0296431 | A1 | 11/2012 | Kim et al. |
| 2013/0079881 | A1 | 3/2013 | Bonassar et al. |
| 2014/0188227 | A1 | 7/2014 | Santerre et al. |
| 2016/0047064 | A1 | 2/2016 | Khandaker et al. |
| 2016/0143745 | A1* | 5/2016 | Kandel ................ C12N 5/0068 623/17.16 |

OTHER PUBLICATIONS

Attia et al., "The response of annulus fibrosus cell to fibronectin-coated nanofibrous polyurethane-anionic dihydroxyoligomer scaffolds", Biomaterials 32, 2011, pp. 450-460.

Bosworth et al., "State of the art composites comprising electrospun fibres coupled with hydrogels: a review", Nanomedicine: Nanotechnology, Biology, and Medicine 9, 2013, pp. 322-335.

Bowles et al., "Tissue Engineering for Regeneration and Replacement of the Intervertebral Disc", Principles of Tissue Engineering, 2014, Chapter 56, pp. 1223-1251.

Bowles et al., "Tissue-engineered intervertebral discs produce new matrix, maintain disc height, and restore biomechanical function to the rodent spine", PNAS, vol. 108, No. 32, Aug. 9, 2011, pp. 13106-13111.

Driscoll et al., "Fiber angle and aspect ratio influence the shear mechanics of oriented electrospun nanofibrous scaffolds", Journal of the Mechanical Behavior Materials 4, 2011, pp. 1627-1636.

Gloria et al., "Dynamic-mechanical properties of a novel composite intervertebral disc prosthesis", J Mater Sci: Mater Med (2007) 18, pp. 2159-2165.

Kim et al., "Notochordal cells stimulate migration of cartilage end plate chondrocytes of the intervertebral disc in in vitro cell migration assays", The Spine Journal 9, 2009, pp. 323-329.

Larraz et al., "Design and Properties of Novel Self-Curing Acrylic Formulations for Application in Intervertebral Disks Restoration", Biomacromolecules, vol. 6, No. 4, 2005, pp. 2058-2066.

Leung et al., "Tissue engineering for intervertebral disc degeneration", Orthopedic Clinics of North America, 2011, v. 42 n. 4, pp. 575-583.

Martin et al., "Translation of an engineered nanofibrous disc-like angle-ply structure for intervertebral disc replacement in a small animal model", Acta Biomaterialia 10, 2014, pp. 2473-2481.

Melrose et al., "Differential Expression of Proteoglycan Epitopes and Growth Characteristics of Intervertebral Disc Cells Grown in Alginate Bead Culture", Cells Tissues Organs, 2001, 168, pp. 137-146.

Mizuno et al., "Biomechanical and biochemical characterization of composite tissue-engineered intervertebral discs", Biomaterials 27, 2006, pp. 362-370.

Mizuno et al., "Tissue-Engineered Composites of Anulus Fibrosus and Nucleus Pulposus for Intervertebral Disc Replacement", SPINE vol. 29, No. 12, 2004, pp. 1290-1298.

Nerurkar et al., "Mechanics of Oriented Electrospun Nanofibrous Scaffolds for Annulus Fibrosus Tissue Engineering", Journal of Orthopaedic Research, Aug. 2007, pp. 1018-1028.

Reitmaier et al., "Hydrogels for nucleus replacement—Facing the biomechanical challenge", Journal of the Mechanical Behavior of Biomedical Material 14, 2012, pp. 67-77.

Ruan et al., "Intervertebral disc transplantation in the treatment of degenerative spine disease: a preliminary study", www.thelancet.com, vol. 369, Mar. 24, 2007, pp. 993-999.

Silva-Correia et al., "Tissue engineering strategies applied in the regeneration of the human intervertebral disk", Biotechnology Advances 31, 2013, pp. 1514-1531.

Smolders et al., "Biomechanical evaluation of a novel nucleus pulposus prosthesis in canine cadaveric spines", The Veterinary Journal 192, 2012, pp. 199-205.

Vadala et al., "Bioactive electrospun scaffold for annulus fibrosus repair and regeneration", European Spine Journal, May 2012, 21 Suppl 1, pp. S20-S26.

Whatley et al., "Intervertebral disc (IVD): Structure, degeneration, repair and regeneration", Materials Science and Engineering C 32, 2012, pp. 61-77.

* cited by examiner

ENGINEERED INTERVERTEBRAL DISC (IVD) FOR DEGENERATED DISC DISEASE

CROSS REFERENCE TO RELATED APPLICATIONS AND CLAIM TO PRIOPRITY

This application claims the benefit of U.S. Provisional Patent Application No. 62/184,298 filed on Jun. 25, 2015 and U.S. Provisional Patent Application No. 62/279,136 filed on Jan. 15, 2016 in the name of Morshed Khandaker et al., which are expressly incorporated herein by reference in their entireties and to which priority is claimed.

STATEMENT AS TO RIGHTS TO INVENTIONS MADE UNDER FEDERALLY SPONSORED RESEARCH OR DEVELOPMENT

This invention was made with government support under Grant Number P20GM103447 awarded by the National Institutes of Health. The government has certain rights in the invention.

FIELD OF THE INVENTION

The present invention generally relates to the field of intervertebral disc (IVD) degeneration and treatment thereof. More specifically, the invention relates to anchorage of nucleus pulposus (NP) gels by aligned electrospun nanofiber mesh that resembles the hierarchical organization of the native annulus fibrosus (AF) and end plate (EP).

BACKGROUND OF THE INVENTION

The intervertebral disc (IVD) is a cartilaginous structure that resembles articular cartilage in its biochemistry, but shows degenerative and ageing changes earlier than does many other connective tissue in the body. This is clinically important because IVD degeneration has been implicated in the etiology of lower back pain in millions of people. Lower back pain is an important socioeconomic disease and one of the most expensive health care issues today. The total cost of the lower back disabilities is in the range of $50 billion per year in the United States. IVD degeneration is caused by the increase of stiffness in nucleus pulposus (NP), bulging of annulus fibrosus (AF) and wearing of end plate (EP) caused by the mechanical overstress to these IVD components, which are shown as a schematic in FIG. 1. Improvements in IVD replacement strategies and materials are a promising, though as yet unrealized therapy for IVD degeneration. NP replacement by viscoelastic gel is emerging as a possible minimally invasive approach for the treatment of degenerative IVD disease. Swelled (hydrogel based material) and unswelled (non-hydrogel based material) NP implants have been investigated by researchers. Both of these NP implants are able to mimic the mechanical behavior of the native nucleus, although they are unable to restore the biomechanical behavior of an IVD.

Discectomy, spinal fusion, and total disc replacement are some of the current surgical treatments to repair degenerated IVD. Discectomy and spinal fusion are complex, costly, and frequently fail to restore the normal biomechanical motion and permanent relieving of the lower back pain of the human spine. There are two types of total disc replacement implants: non-tissue engineered and tissue engineered. Non-tissue engineered total disc replacement implants use a combination of metal and polymers to replacement degenerated disc. There are only two FDA approved implants: SB Charite and ProDisc are currently available in the market. Among the problems of the non-tissue engineered total disc replacement implants are that they often lead to mechanical failure, dislodgement, wear, and associated osteolysis and implant loosening. Tissue engineered total disc replacement implants use the principles of cell biology to determine the nature of the NP, AF and cartilage cells at EP, to create composite scaffolds for each of the components of IVD. The ability of AF cells to remodel and grow in fibrous matrices, as well as the ability of NP cells to assemble hydrogel based extracellular matrix have lead to the fabrication of IVD implants to regenerate AF and NP tissue as a unit. Despite the promise of tissue engineering approaches for design of IVD implants (only one FDA approved implant: Raymedica prosthetic disc nucleus (PDN)), to date no tissue engineered IVD has demonstrated the long term load bearing capability that is equivalent to a native disc. Currently researched tissue-engineered IVD lacks in withstanding the long-term physiological load (cyclic load). Tissue-engineered IVD assembled in the shape of cylindrical disks composed of an outer shell of fiber mesh seeded with annulus fibrosus cells with an inner core of nucleus pulposus cells seeded into gel lack in effectiveness because proper anchorage of the top and bottom sides of IVD is ignored. Bowles et al. in vivo study showed that tissue-engineered IVD, composed of gelatinous NP surrounded by an aligned collagenous AF, can maintain disc space height, produced de novo extracellular matrix, and integrated into the spine, yielding an intact motion segment with dynamic mechanical properties similar to that of native IVD. This study suggested that if a tissue engineered IVD is designed properly, it does not need to be seeded with cells for functioning of the disc. There is no in vivo study reported showing tissue-engineered IVDs withstanding the long-term physiological load. Proper anchorage of NP and AF is required for a successful IVD design, since IVD needs to carry significant deformations even under relatively low-loading conditions and needs mechanical stability for long term physiological loads. Therefore, a tissue and non-tissue engineered IVD construct must include the top and bottom anchorage, which may constitute EP architecture, to NP and AF when engineered IVD is implanted in a human body.

The intervertebral disc (IVD) is one of the body's most vital structures. The nucleus pulposus (NP) in IVD is restricted axially by the superior and inferior cartilaginous endplates (EP) and circumferentially by the annulus fibrosus (AF). It is reported that the mechanical role of the NP is to resist and redistribute compressive normal and shear forces within the spine, whereas the major function of the AF is to withstand tension normal and shear forces. The AF that comprises discrete fibrous sheets with specialized collagen alignment endures multi-directional loads around the circumference. Fibers run in a single direction in native AF tissue, ranging from 20° to 50° with respect to the transverse plane, and adjacent lamellae have opposing fiber orientations, producing an angle-ply structure. Endplates significantly contribute to mechanical characteristic of NP even under relatively low-loading condition. Despite the intensive research over the past decade directed to IVD materials, there is not yet any material that can reproduce adequately the physiological, mechanical and biological behavior of the natural IVD, and at the same time exhibit long-term biomechanical functionality when introduced into the human spine. An IVD implant is needed to restore the spine from instability due to IVD degeneration. A method is needed to provide effective anchorage of an NP implant and improve the mechanical stability of the IVD implant after nucleotomy.

SUMMARY OF THE INVENTION

The present invention provides a novel process to produce electrospun nanofiber-anchored NP gels and a functional design for novel engineered IVD. The present invention provides a process by which both non-tissue engineered and tissue engineered cartilaginous-like structures can be fabricated. The disclosed invention provides a method for fabrication of both non-tissue and tissue engineered IVDs. These engineered IVD structures can be used to produce replacements for degenerated natural IVD. One aspect of the present invention is the use of PCL electrospun nanofiber (ENF) mesh to anchor the NP gel to withstand multi-directional loads. The nanofibers produced are typically in the range of 50 to 1000 nanometers in diameter. In another aspect, the method of the present invention can create angle-ply AF structure around the circumference of NP gels to mimic the architecture of natural IVD substantially replicating at least biomechanical behavior of the annulus fibrosus (AF). The angle-ply AF structure comprises layers of ENF aligned substantially parallel in the same plane (aligned fibers), where the aligned ENF comprising each layer is positioned at an angle to the aligned ENF comprising adjacent layers. In another aspect, the method of the present invention can be utilized to anchor the top and bottom sides of NP gels by using non-woven aligned or random fiber mesh to create a scaffold for the generation of endplate (EP) tissue substantially replicating at least biomechanical behavior of the superior and inferior cartilaginous endplates (EP) of a natural IVD.

The present invention provides a novel method to accomplish anchorage of NP gels by utilization of aligned electrospun nanofiber mesh that resembles the hierarchical organization of the native AF and EP. The present invention provides an engineered NP gel anchored by an electrospun nanofiber scaffold mimicking AF and EP structure and produces an engineered IVD that can restore the biomechanical performances of the degenerated natural IVD after a nucleotomy. After implanting engineered IVD produced by the methods provided by the process of the present invention into animal tail ex vivo and conducting mechanical tests on the samples, the range of motion and stiffness at different directions of load measured using a mechanical test system were observed to mimic natural IVD performance. Bovine and rabbit tail were used in the laboratory for such tests. The present invention provides a method for use of both swelled and unswelled NP gels anchored by tissue cultured electrospun nanofiber mesh mimicking AF and EP architectures for total IVD implant, where such engineered IVD can restore biomechanical functions of native disc after nucleotomy.

The present invention provides a novel IVD implant able to restore the spine from instability due to IVD degeneration. IVD degeneration and instability is a very common process in the aging of the human population, basically due to dehydration and increasing stiffness of NP, and bulging of AF caused by mechanical overstress to the natural IVD components. IVD provides support and enables six degree of freedom (6 DOF) motions to the spine. The motions are flexion, extension, right and left lateral bending, compression, and axial rotation as schematically shown in FIG. 2. When individuals suffer from degenerative disc disease, the NP deteriorates, causing a loss of 6 DOF motions in the IVD and producing lower back pain. Lower back pain is generally associated with degeneration of the lumbar IVD. The present invention provides a method for producing an engineered IVD (EIVD) for use as total disc replacement material to relieve pain and restore normal spinal motion. The present invention provides a method to create novel composite tissue-engineered IVD implants, where electrospun AF and EP fibrous are coupled with a NP gel to satisfy long term biomechanical functions replicating a native disc.

Electrospun nanofibers and hydrogels are commonly exploited because of their ability to mimic natural tissues; however, their clinical use remains restricted due to negligible cellular infiltration and poor mechanical properties, respectively. To date, very limited research has been conducted to investigate composite scaffolds based on electrospun nanofibers and hydrogels in an attempt to overcome their individual shortcomings. The method of the present invention illustrated generally in FIG. 3 uses the electrospinning process illustrated in FIG. 10 to generate angle-ply nanofiber structures that substantially recreate the organized fibrous architecture of native AF. Single strips of aligned nanofiber scaffold are arranged concentrically around an NP gel at alternate angles (Position A and Position B in FIG. 10), closely mimicking the alternating fiber alignment of native tissue, to form disc-like angle-ply nanofiber structures. Experimental results demonstrate these constructs mature both compositionally and mechanically over time in culture, indicating their potential for use in total disc replacement. Prior to the method provided by the present invention there has been no method developed to anchor NP along the AF and EP directions by electrospun nanofiber mesh that can withstand physiological loading. Using the methods of the present invention, effective anchorage can be produced that satisfies the long term biomechanical functions required of an IVD including tension normal and shear forces. In previous research, the present inventor et al. successfully developed novel electrospin processes [co-pending U.S. patent application Ser. No. 14/734,147, International Patent Application No. PCT/US15/45183, and U.S. Pat. No. 9,359,694] that may be used to produce aligned electrospun nanofiber mesh as implemented in the present invention. Aligned nanofiber mesh structures as implemented in the present invention may cover the sides of the NP gel so that no NP gel will spill out under load from the nanofiber mesh. In this way, the aligned nanofiber mesh can be used to anchor NP gels, producing AF and EP scaffolds.

The IVD developed using the method of the present invention, based upon mechanical and ex vivo experiments, shows the potentiality of the developed IVD for a non-tissue engineered IVD or a tissue engineered IVD. In a separate study, bi-direction electrospun poly (e-caprolactone) (PCL) nanofiber scaffolds were produced and the scaffolds seeded with osteoblast cells [co-pending U.S. patent application Ser. No. 14/734,147, International Patent Application No. PCT/US15/45183, and U.S. Pat. No. 9,359,694]. Engineered IVD were implanted in bovine and rabbit tails for ex vivo lab tests. Mechanical tests on the implant samples were conducted to determine the range of motion and stiffness at different direction of loading using a mechanical test system. These studies showed electrospun nanofiber scaffolds with aligned nanofibers permit cell attachment and promote directed matrix production. The present invention provides a method that uses electrospun nanofiber to produce an engineered IVD that can restore biomechanical functions after nucleotomy. The biomechanical performance of these IVDs having electrospun nanofiber mesh in every side of NP exceeds those of an IVD made with NP covered circumferentially by AF fiber mesh only, providing functional replacement models for natural IVD.

Nucleus replacement aims at replacing only the degenerated nucleus, keeping the remaining disc structure intact. The NP substitution by polymeric gel is one of the promising techniques for the repair of degenerated natural IVD. Numerous swelled and unswelled polymeric gels have been investigated as a suitable material for NP. In developing the present invention, research was conducted to investigate a swelled gel (polyvinyl alcohol (PVA)-polyvinyl pyrrolidone (PVP)) and an unswelled gel (silicone), all of which are potential NP replacement materials. Swelled gel (often referred as hydrogel) is the most widely researched NP implant for degenerated IVD. NP cells can be mixed with hydrogel to produce tissue engineered NP. The present invention provides an IVD construct where NP cell seeded hydrogels can be injected into a chamber made by AF and EP fibrous layers. Hydrogels are available from suppliers such as Sigma-Aldrich, LLC, St. Louis, Mo. The advantage of unswelled gel is that, when cured, it is moldable, highly cohesive and suitable for long term body implantation. Without an appropriate annulus closure the displacement of the gel material can cause damage into the inner annulus under physiological loading conditions, which characteristic makes them singularly inappropriate materials for IVD restoration. The present invention provides an IVD construct comprising electrospun nanofibers coupled with swelled and unswelled hydrogels having similar viscoelastic nature for restoring capability of the native disc biomechanics. Use of a plurality of suitable gel or gel-like materials for engineered IVD application is anticipated, as well as PCL alternatives. Implantable medical grade silicone and Polyethylene (glycol) Diacrylate (PEGDA) are preferred gels usable in the present invention. Silicone gel may be prepared by mixing a 40 wt % of poly-dimethyl-hydogen-siloxane crosslinker agent with polydimethylvinylsiloxane base. Both the base and crosslinker are available from Applied Silicone Corporation, Santa Paula, Calif. PEGDA is available from suppliers such as Sigma-Aldrich Co. LLC. PEGDA is a blank slate hydrogel that gels rapidly at room temperature in the presence of a photo-initiator and UV light. PEGDA is hydrophilic, elastic and can be customized to include a variety of biological molecules. In addition, the methods provided by the present invention can be used to construct electrospun nanofiber mesh as scaffolds for constructing cartilaginous-like structures in a plurality of applications where restoration or replacement of articular cartilage is needed.

DETAILED DESCRIPTION OF PREFERRED EMBODIMENTS OF THE INVENTION

The present invention provides a process by which both non-tissue engineered and tissue engineered cartilaginous-like structures can be fabricated. The process of the present invention provides a method to produce electrospun nanofiber-anchored NP gels. The present invention provides a functional design for novel engineered IVD. The present invention provides a method for fabrication of both non-tissue and tissue engineered IVDs. These cartilaginous-like structures are used to produce replacements for degenerated natural IVD. The method of the present invention can use electrospun PCL nanofiber mesh to anchor the NP. The method of the present invention can create angle-ply AF structure around the circumference of NP to mimic the architecture of native IVD. The method of the present invention effectively anchors the top and bottom sides of NP by using non-woven aligned or random nanofiber mesh produced by electrospining nanofibers to create a scaffold for the generation of endplate (EP) tissue. The method of the present invention that produces an engineered IVD is illustrated in FIG. 3 through FIG. 12 and described below.

Figure 1:
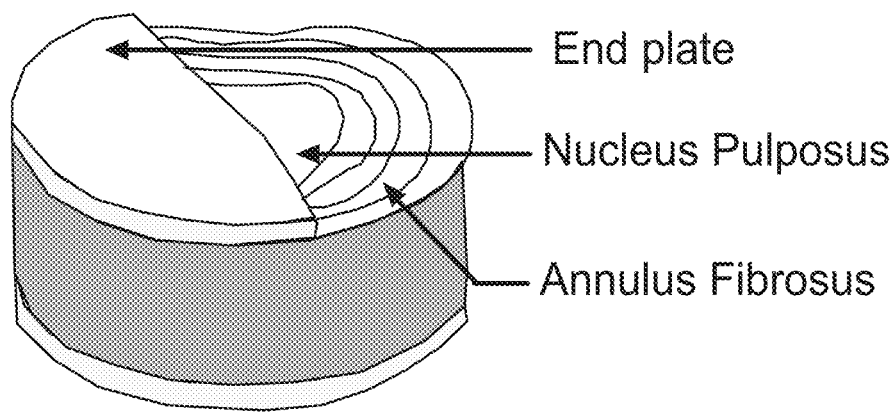
FIG. 1 is a non-limiting diagram showing a schematic representation of different components of natural IVD.
Figure 2:
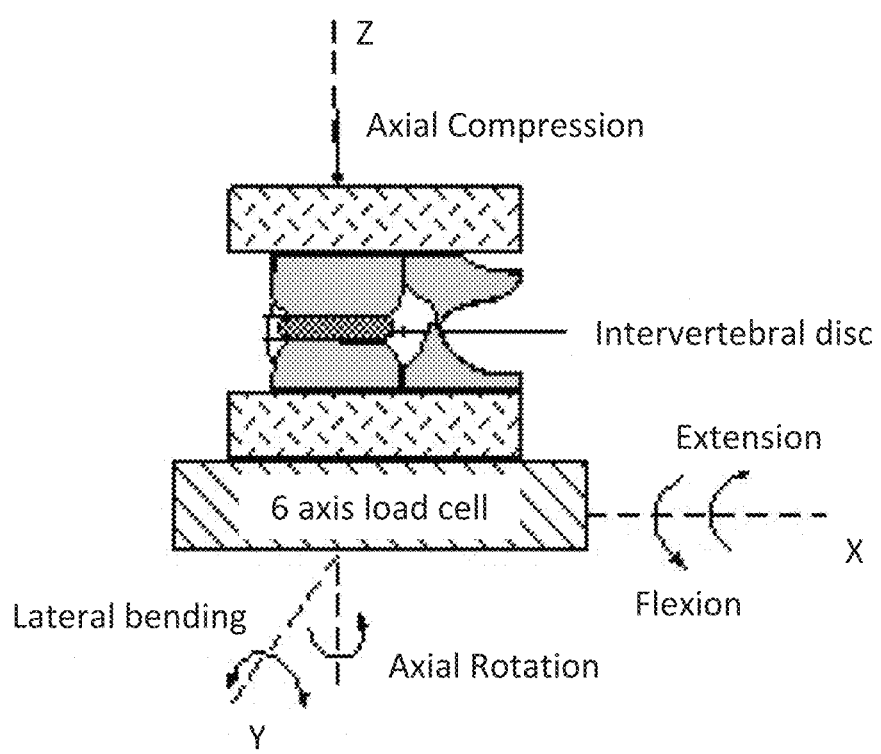
FIG. 2 is a non-limiting diagram showing a schematic representation of the in-vitro biomechanical testing of human lumbar spine segments under compression, flexion-extension, lateral bending and rotation motions.
Figure 3:
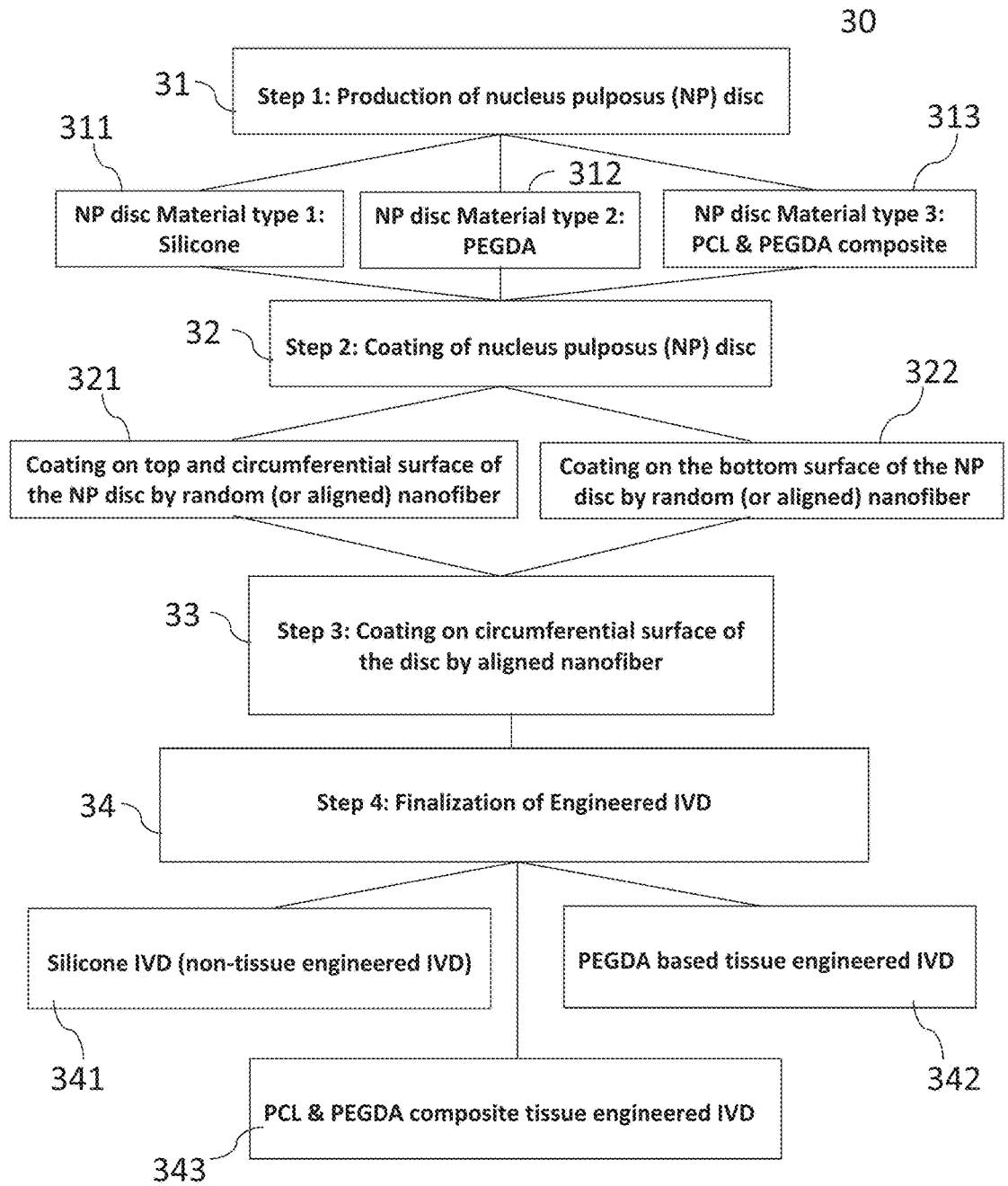
FIG. 3 is a non-limiting diagram showing generally the method of the present invention.

Referring now to FIG. 3, the methods of the present invention 30 to produce an engineered IVD are shown as four principal steps, which steps are further illustrated in FIG. 4 through FIG. 12 and disclosed herein:

31 Step 1: Production of nucleus pulposus (NP) disc using one of silicone 311, PEGDA 312, or layered PCL nanofiber and PEGDA composite 313.

32 Step 2: Coating one surface (e.g., top) and the circumferential surface of the NP disc applying randomly deposited electrospin PCL nanofiber 321, followed by coating a second uncoated surface (e.g., bottom) applying randomly deposited electrospin PCL nanofiber 322.

33 Step 3: Coating on circumferential surface of the NP disc applying substantially parallel aligned electrospun PCL nanofiber to construct a mesh structure (see FIG. 10).

34 Step 4: Finalization of Engineered IVD where one of silicone 341, PEGDA 342, or PCL nanofiber & PEGDA composite 343 comprises the NP material.

Figure 4:
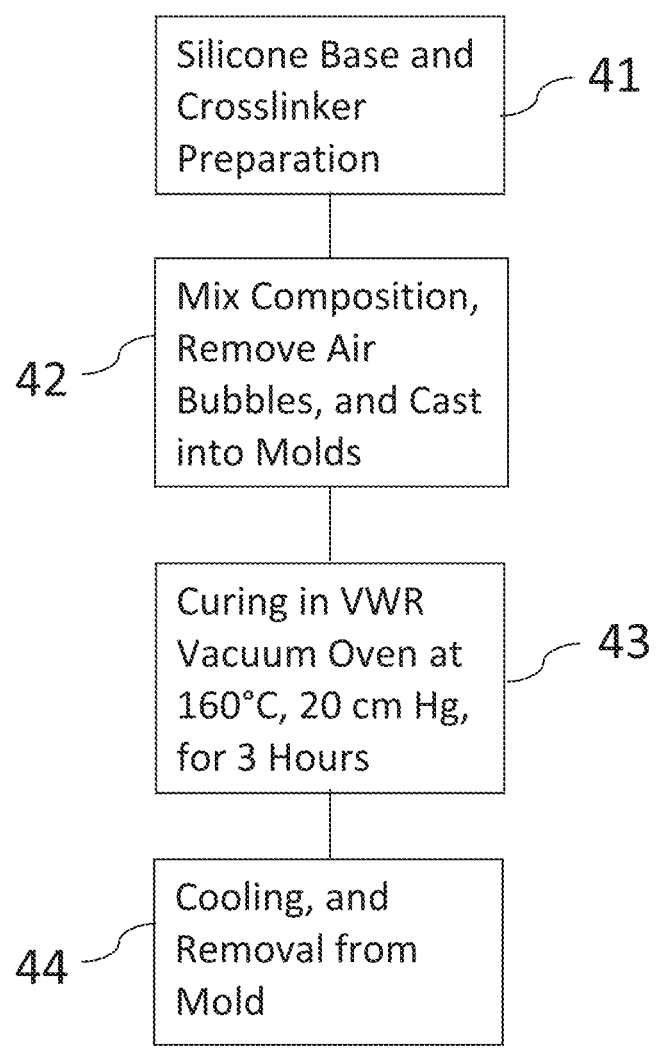
FIG. 4 is a non-limiting diagram showing the silicone synthesis and Disc Procedure of the present invention.

Referring now to FIG. 4, a process 40 is shown for performing (FIG. 3, 311) Step 1: Production of nucleus pulposus (NP) disc selecting NP disc Material type 1: silicone (implant grade).

Materials

The materials 41 used for the silicone synthesis may include responsive silicone gel system base (implant grade), and responsive silicone gel system crosslinker (implant grade). The silicone gel system may be fabricated to model the nucleus pulposus of the intervertebral disc (IVD). Silicone gel may be prepared by mixing 41 a 40 wt % of poly-dimethyl-hydogen-siloxane crosslinker agent with polydimethylvinylsiloxane base to produce a high strength silicone gel system (implant grade). The compressive strength should be in the range of 36 kPa to 40 kPa and preferably 38.75 kPa. The shear modulus should be in the range of 250 Pa to 300 Pa and preferably 270 Pa. The preferred compressive strength and shear modulus can be achieved when 83 wt % of cross-linker agent is used. Both base and cross-linker are available from Applied Silicone Corporation, Santa Paula, Calif.

Instrumentation

Instrumentation that may be used for the silicone synthesis includes a 100 mL beaker, VWR® Vacuum Oven (available from VWR International, Radnor, Pa.), VWR® single channel pipette (variable volume) (available from VWR International, Radnor, Pa.), curing mold (aluminum), glass stirring rod, and an analytical balance.

Method

Figure 4A:
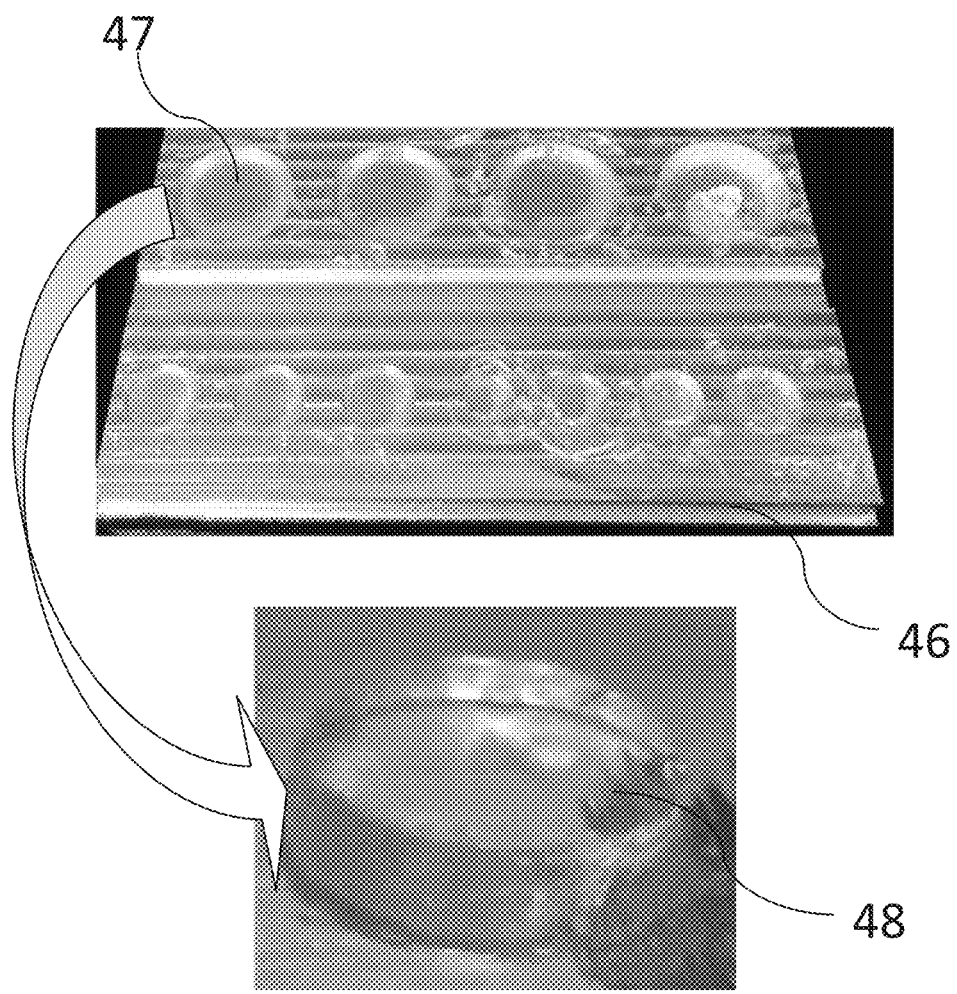
FIG. 4a is a non-limiting image showing a mold (top image) used to cure silicone to prepare silicone discs, and a produced silicone disc removed from the mold (bottom image).

In a preferred silicone synthesis process 40, the silicone may be prepared 41 using manufacturer instructions (e.g., a 73.2% to 26.8% by weight ratio of silicone system base and silicone system crosslinker, respectively). The silicone base and silicone crosslinker may be weighed and measured with a scale and VWR® pipette, then mixed 42 in 100 mL beaker for 20 minutes. The solution may be stirred manually with a glass stirring rod. The solution may then be placed in the VWR® Vacuum Oven for 10 minutes at 20 cm Hg vacuum to remove air bubbles 42 from the solution. Once air bubbles are removed, the silicone solution may be removed from the oven and cast 42 into a curing mold (see FIG. 4a, 46) with the use of the VWR® pipette (available from Cole-Parmer Instrument Company, Bunker Court Vernon Hills, Ill.). The curing mold (FIG. 4a, 46) may then be placed in the VWR® Vacuum Oven 43 preferably at 160° C. and 20 cm Hg for 3 hours for curing. The molded silicone (FIG. 4a, 47) should be allowed to cool and removed from the oven 44. The resulting silicone disc model (FIG. 4a, 48) may be removed from the curing mold in preparation for nanofiber application 44. The inventor has successfully fabricated 10 mm diameter and 5 mm thickness silicone gel (see FIG. 4a) using the preferred process 40 of the present invention (FIG. 3, 30). Larger diameters are anticipated and possible using the process 40 and a mold configured with larger diameter cavities.

Figure 5:
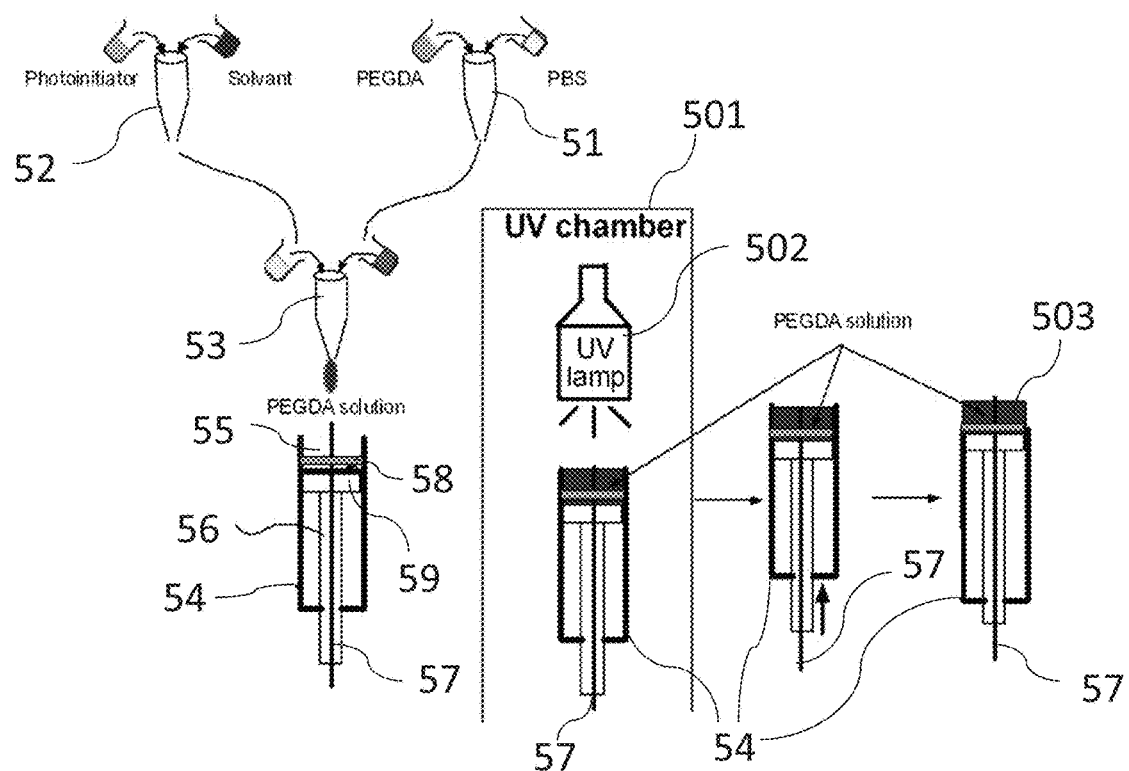
FIG. 5 is a non-limiting diagram showing the PEGDA Synthesis and Disc Procedure of the present invention.

Referring now to FIG. 5, the process 50 is shown for performing a preferred method (FIG. 3, 312) Step 1: Production of nucleus pulposus (NP) disc selecting NP disc Material type 2: PEGDA.

Materials

Two solutions, PEGDA ($M_n$=700; source Sigma-Aldrich, LLC) with the Phosphate Buffer Solution (PBS) solvents, and the photo initiator (PI), Alpha-alpha-dimethoxy-alpha-phenylacetophenone ($M_w$=256.35 g/mol; source Sigma-Aldrich, LLC) with the 1-vinyl-2-pyrrolidone ($M_w$=111.14 g/mol; Fluka) solvents, may be used to fabricate preferred gel solutions. PBS may also be used instead of water in this process to produce preferred gels, since PBS is a better biological solvent than water when preparing cell encapsulating PEGDA gel (FIG. 3, 312).

Method

FIG. 5 shows the steps of a preferred method that may be used for the preparation of the mold and specimen. 20% PEGDA in PBS mixture 51 may be added to the 0.2% concentration of photoinitiator mixture 52 to prepare the PEGDA solution 53. The PEGDA solution may then be poured in a plastic syringe 54 configured with a chamber 55, where there is a through hole fabricated at the center of the plunger 56. The hole is used to support a conductive wire 57. A silicone pad 58 (available from Casting Craft Easymold Silicone Rubber, Environmental Technology Inc. Fields Landing, Calif.) may be glued on the top of the plunger pushing rod 59. The silicone pad 58 prevents leakage of PEGDA solution from the syringe chamber 55. A conductive wire 57 may be inserted through the plunger hole up to the top of the syringe chamber 55. The solution may then be poured into the syringe chamber 55 to cure the mixture in a round shape gel. The photo-polymerization system 501 used in preferred embodiments of the present invention (FIG. 3, 30) is comprised of three major parts: a UV light source 502, the plastic syringe 54, and a polymer solution inside the syringe chamber 55. The role of the plastic syringe 54 is to mold and allow the PEGDA to polymerize in the desired shape. The solution may be polymerized by exposure to long wave UV light for at least 3 minutes. One preferred equipment for use in PEGDA polymerization is a 365 nm long wave UV lamp Model B-100SP Ultraviolet Lamp, available from UVP, LLC. Other UV Lamps may also be used in the method. After polymerization, the syringe chamber 55 may be extracted from photo-polymerization system 501, and plunger 59 may be used to push out and free the PEGDA disc 503 from the syringe chamber 55. Using the processes of the present invention (FIG. 3, 30) implementing the preferred photo-polymerization system 501 (depicted in FIG. 6), the inventor has successfully fabricated 10 mm diameter and 3 mm thickness PEGDA discs 503 (see FIG. 6). Larger diameter PEGDA discs are anticipated and possible using a larger diameter syringe chamber.

Figure 7:
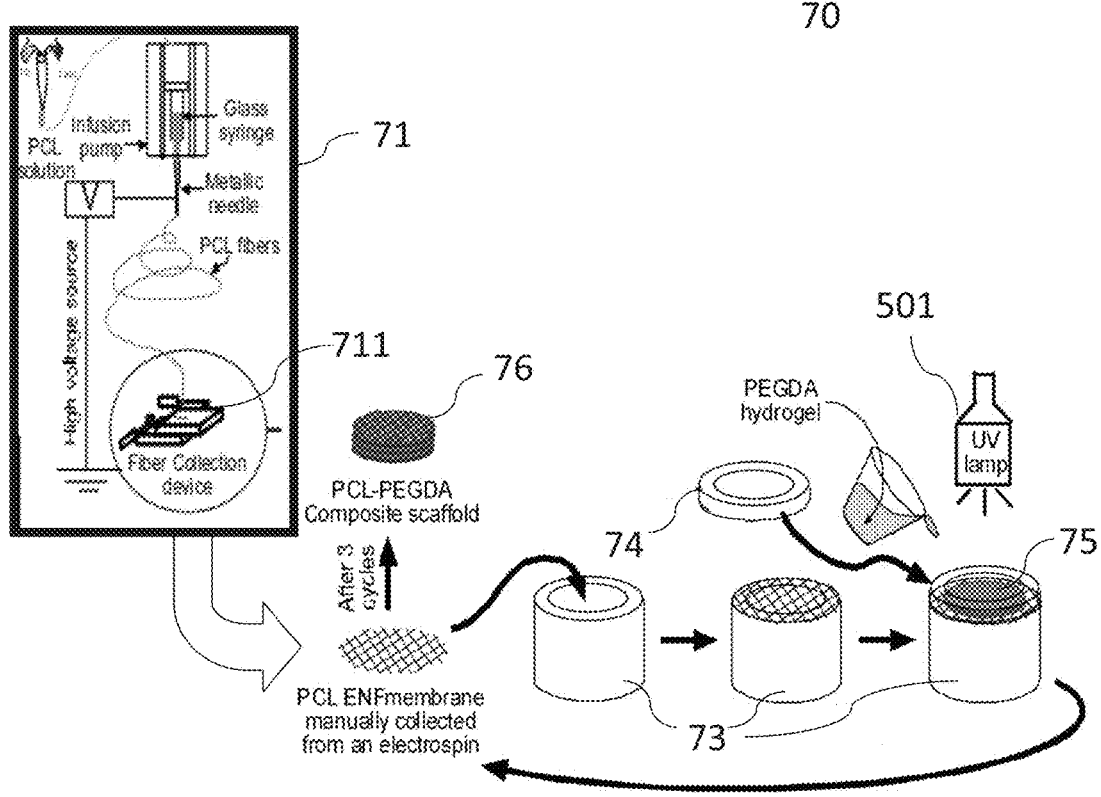
FIG. 7 is a non-limiting diagram showing the process of the present invention applied in creating a composite scaffold made with 4 layers of PCL electrospun nanofiber (ENF) membrane and 3 layers of PEGDA hydrogel.

Referring now to FIG. 7, the process 70 is shown for performing (FIG. 3, 313) Step 1: Production of nucleus pulposus (NP) disc selecting NP disc Material type 3: PCL & PEGDA composite disc, the composite comprising PCL nanofiber and PEGDA.

Materials

Poly(ε-caprolactone) (PCL) solution may be prepared by mixing PCL pellets (pellet size-3 mm, average Mn 80,000) with acetone (laboratory reagent≥99.5%). Both PCL and acetone are available from Sigma Aldrich (Sigma-Aldrich Co. LLC., St. Louis, Mo.). PEGDA solution may be prepared according to the method previously described above.

Method

The process 70 of the present invention (FIG. 3, 30) shown schematically in FIG. 7 produces a composite scaffold that combines layers of electrospin nanofibers (ENF) with alternating layers of PEGDA hydrogel. In a preferred method a composite scaffold may be made combining 4 layers of PCL ENF membrane and 3 layers of PEGDA hydrogel. Three or more layers of PEGDA-PCL composite scaffold may be fabricated using a manually operated or automated electrospin setup 71 following the process 70 sequence and using the UV photo-polymerization unit 501 shown in FIG. 6. Using the electrospin setup 71, aligned PCL ENF with fibers aligned substantially parallel may be produced and intercepted between two parallel collectors 711. The fibers produced using the setup 71 range from 305 nanometer diameter fiber to 585 nm diameters. The length of PCL ENF produced using the dual wire setup 112 shown in FIG. 10 was typically 50 mm. Longer fibers can be produced and the diameters adjusted using the methods and apparatus disclosed in U.S. Pat. No. 9,359,694. The longer fibers may be used in the preferred methods of the present invention to produce larger diameter engineered IVD, as well as engineered cartilaginous structures in a plurality of shapes and sizes. To collect multiple layers of fiber 72, an acrylic hollow cylindrical substrate 73 may be used to touch the aligned fiber stream intercepting the fibers produced by the electrospin setup 71. The substrate 73 may then be lowered and rotated by 90° and the process repeated to collect another layer of fibers 72 aligned substantially parallel to each other and substantially orthogonal to fibers comprising the previous layer, creating a non-woven fabric. A silicone mold or a hollow cylindrical mold 74 (preferably thickness=0.5 mm and inside diameter at least 10 mm) may be used to cure hydrogel according to the required shape of the composite hydrogel to be produced. PEGDA may be injected in the mold on top of PCL ENF membrane to build the composite scaffold 75. The same UV light source 501 used to create PEGDA disc (see FIG. 5, 503) when exposed to the solution will cure the PEGDA solution to solid. The thickness of the PEGDA layer of the scaffold 75 produced may be in the range of 0.3 mm to 0.7 mm with 0.5 mm being preferred. The forgoing ENF membrane and PEGDA curing steps may be repeated three or more times to make 1.0 mm to 5.0 mm thick cylindrical composite scaffold 76 with 1.5 mm to 3 mm being preferred. The inventor has implemented the preferred methods provided by the process of the present invention to successfully fabricate 10 mm diameter and 3 mm thickness PCL nanofiber and PEGDA composite disc (depicted in FIG. 6, 503). Larger diameter composite discs are also anticipated using the methods disclosed herein, as well as using the apparatus of U.S. Pat. No. 9,359,694.

Figure 8:
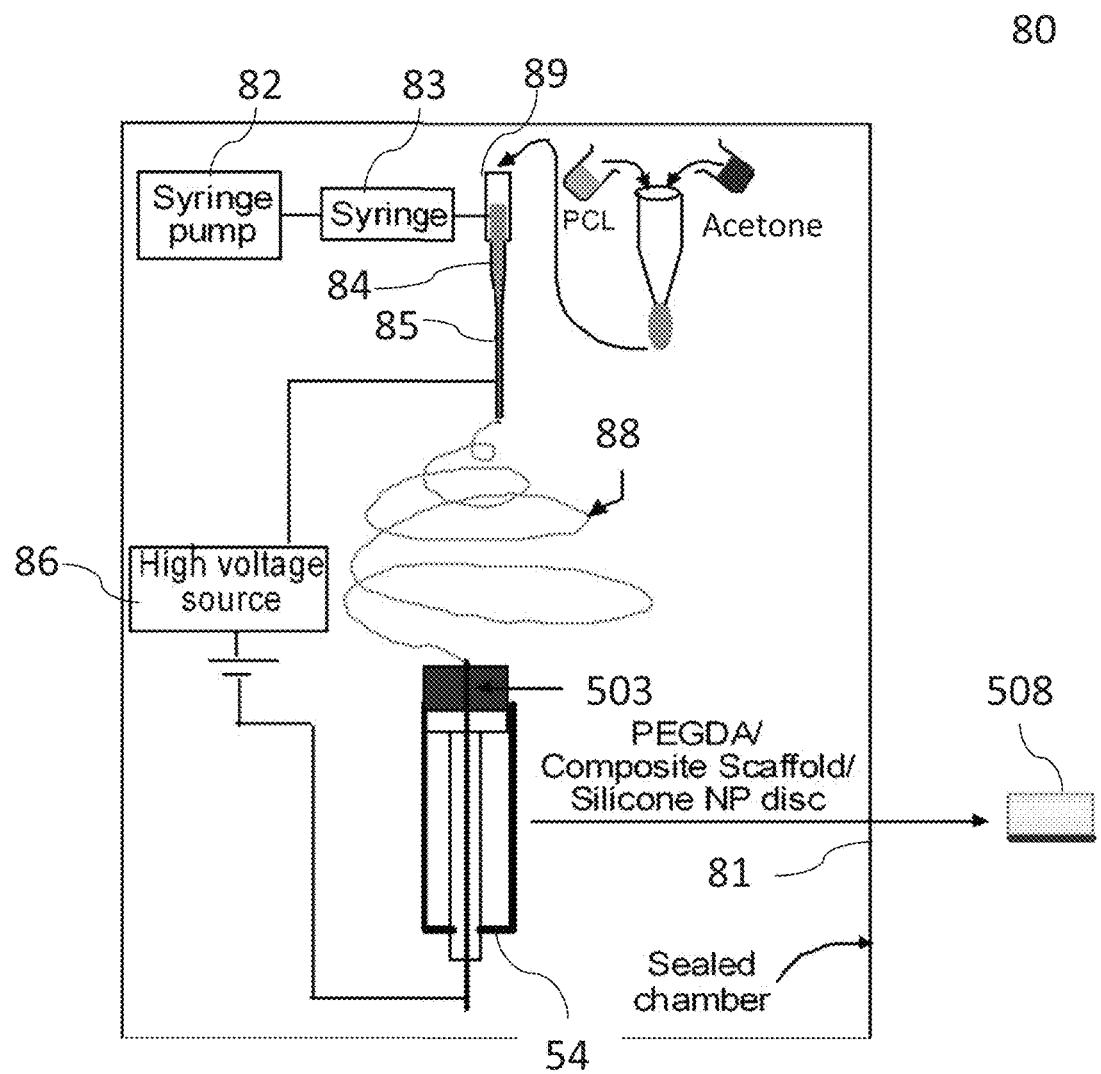
FIG. 8 is a non-limiting diagram showing the process of the present invention for coating an NP disc on top and circumferential sides with randomly applied nanofiber.

Referring now to FIG. 8, the process 80 is shown for performing (FIG. 3, 321) Step 2: Coating one surface (e.g., top) and the circumferential surface of the NP disc with electrospin random nanofiber. In Step 2 of the process of the present invention, NP disc 503 produced in the plastic syringe 54 may be coated with randomly applied PCL nanofiber 88 at a first side (e.g., top) and at circumferential sides by multiple layers of randomly applied nanofiber to produce a coated disc 508 where the thickness of the nanofiber layers comprising the first applied coating is in the range of 1 to 6 microns and preferably at least 2 microns. FIG. 8 shows the process for coating of NP disc by randomly deposited PCL nanofibers on a first side (e.g., top) and on circumferential sides. The embodiment shown in the diagram includes the sealed chamber 81, a syringe pump 82, a syringe 83 with a tube 84 that is attached with a non-conducting support 89, a syringe needle 85 at the end of the tube 84, a high voltage power supply 86, and a plastic syringe 54 containing the NP disc 503. The syringe needle 85 is electrically charged by applying a high-voltage in the range of (5 KVA to 15 KVA) produced by the power supply 86. Negative charge is applied to the conductive wire 57 positioned through a hole extending longitudinally through the push rod 56 centered in the syringe 54.

Figure 9:
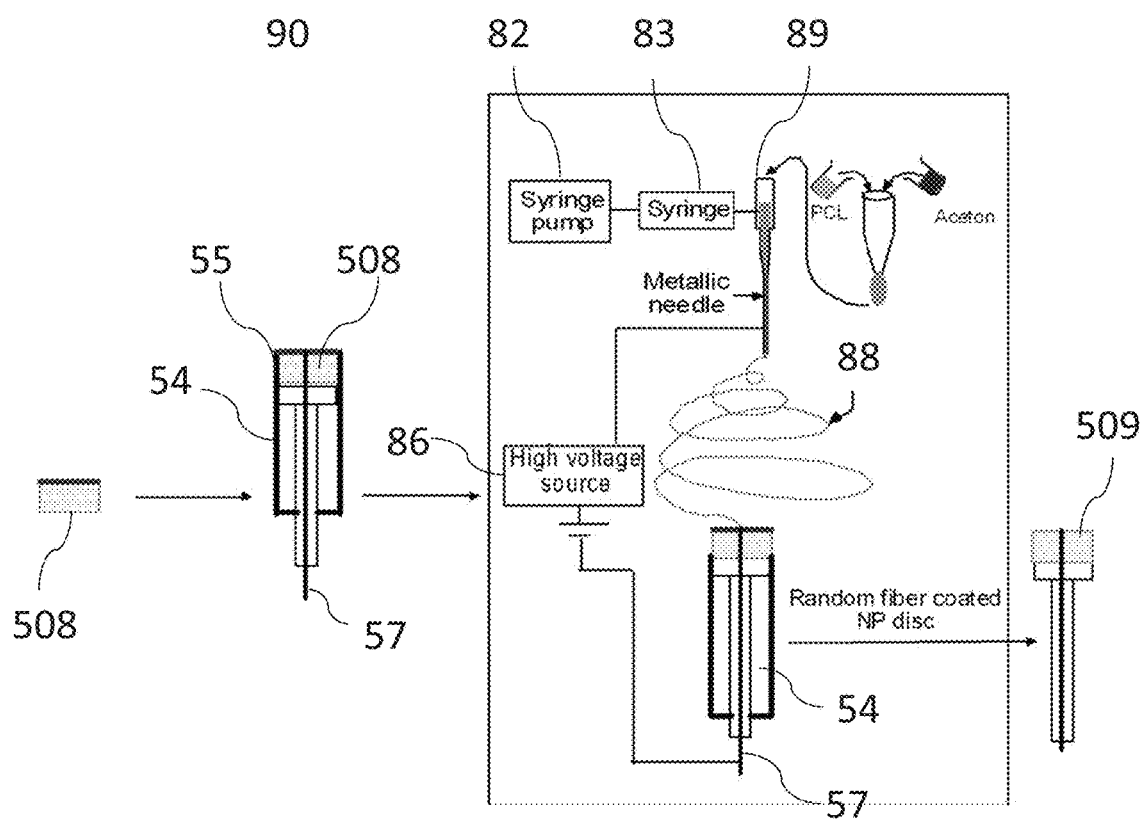
FIG. 9 is a non-limiting diagram showing the process of the present invention for coating the bottom surface of the NP disc with randomly applied nanofiber.

Referring now to FIG. 9, the process 90 is shown for performing (FIG. 3, 322) Step 2: Coating on a second uncoated side (e.g., bottom) surface of the NP disc 508 with electrospin randomly applied nanofiber 88. In Step 2 of the process of the present invention (FIG. 3, 30), the partially coated NP disc 508 may be inverted and placed in the plastic syringe 54 with the conductive wire 57 inserted through the center. The NP disc 508 is placed again in the plastic chamber 55 with the conductive wire 57 inserted at the center. The bottom side of NP disc 508 that didn't have PCL fiber mesh coating applied is face up so that randomly applied nanofiber 88 can be coated on that side. The uncoated side (e.g., bottom) of the NP disc 508 may be coated with multiple layers of randomly deposited PCL fiber 88 to produce a coated NP disc 509 where the second applied coating is in the range of 5 to 15 microns and preferably at least 10 microns. FIG. 9 shows the process by which an NP disc 509 may be coated by randomly deposited fibers on the side where there is no existence of fiber coating.

Figure 10:
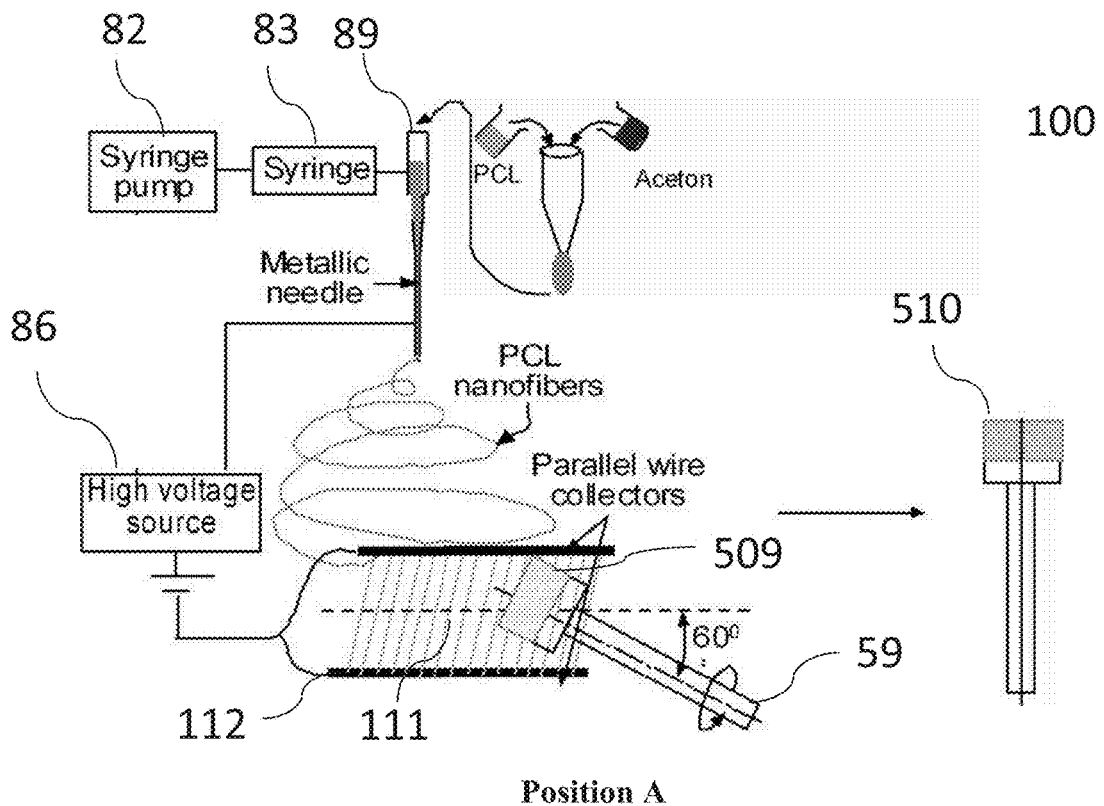
FIG. 10 is a non-limiting diagram showing the methods of the present invention for production of an angle-ply nanofiber structure on the circumference of an NP disc where the angle-ply structure is produced by intercepting parallel aligned ENF at alternate angles at Position A and Position B.
Figure 10:
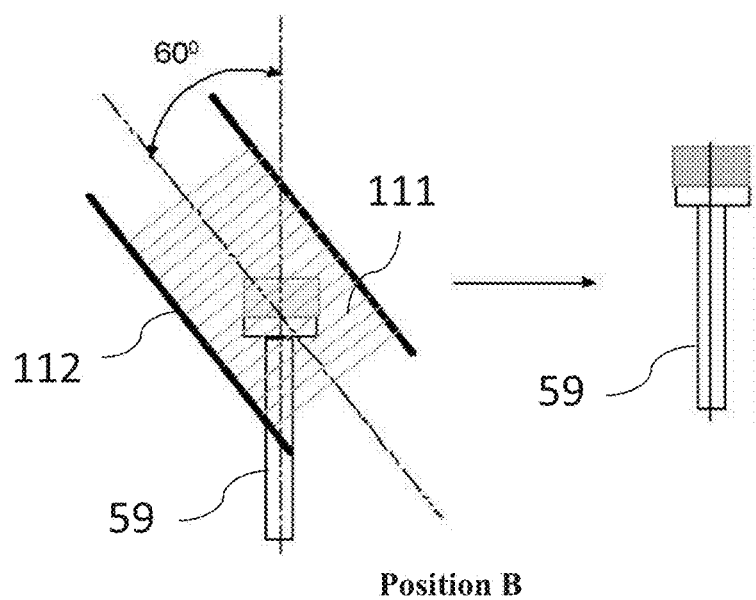
Figure 11:
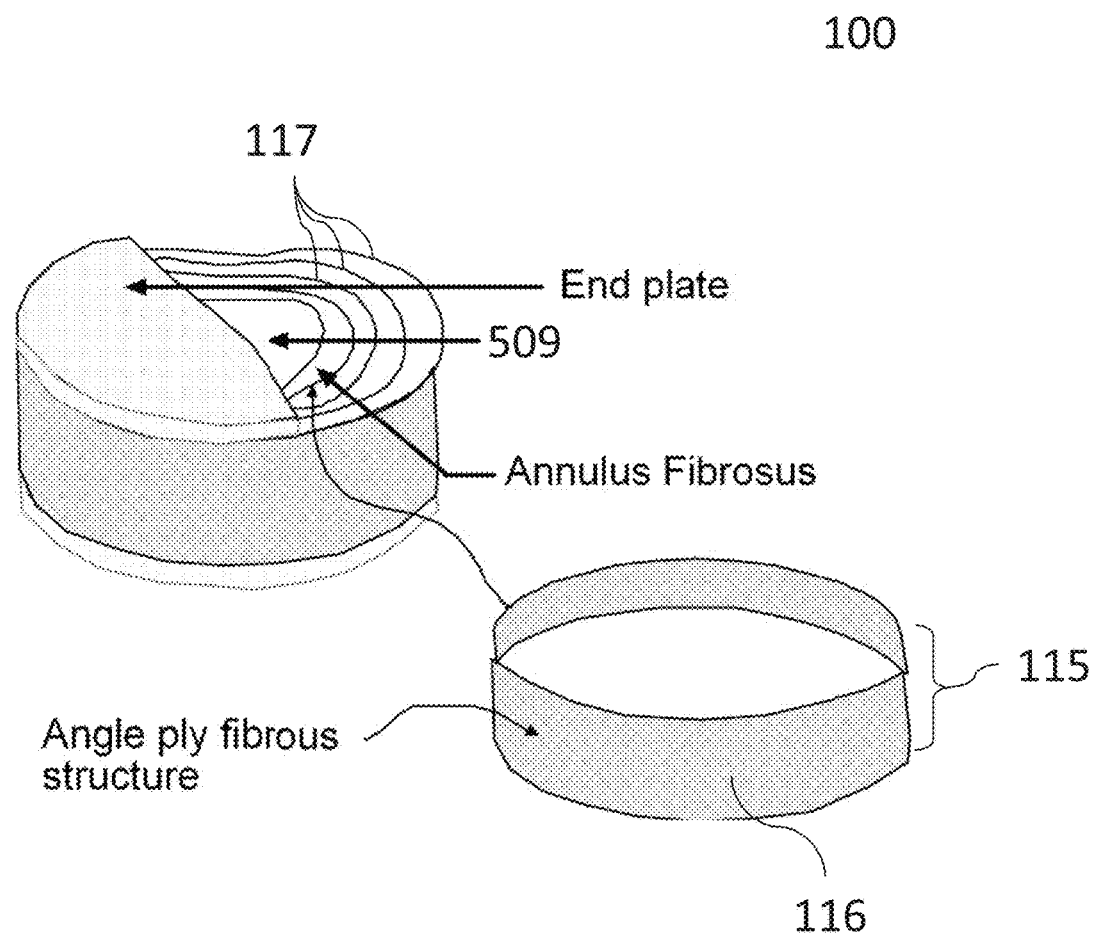
FIG. 11 is a non-limiting diagram showing components of an engineered IVD produced using methods of the present invention where the components of the engineered IVD mimic the architecture of a natural IVD.

Referring now to FIG. 10, the process 100 is shown for performing (FIG. 3, 33) Step 3: Coating on circumferential surface of the disc by aligned nanofiber structure. The process of the present invention (FIG. 3, 30) concludes with the NP disc 509 being completely encased with an electrospun nanofiber membrane to support various types of NP disc applications. The NP disc 509 is wrapped with an angle-ply band constructed of aligned electrospin nanofibers in multiple layers where the fibers in one layer are angled at an oblique angle in the range of 40 to 80 degrees and preferably 60 degrees with respect to fibers in adjacent layers to mimic natural IVD annual fibrous (AF) as shown in FIG. 11. The AF that comprises discrete fibrous sheets endures the multi-directional loads around the circumference of a natural NP disc. In preferred embodiments, PCL nanofibers can be mixed with collagen solution to increase the stiffness of the nanofiber mesh. Natural fibers run in a single direction in native AF tissue, ranging from 20° to 60° with respect to the transverse plane, and adjacent lamellae have opposing fiber orientations, producing a natural angle-ply structure.

The process 100 of the present invention (FIG. 3, 30) provides at least two ways the angle-ply fibrous structures 115 as depicted in FIG. 11 can be produced along the circumference of the NP disc 509 to produce the completed NP disc 510. The preferred method is to rotate the NP disc 509 attached to the plunger pushing rod 59 at oblique angles, preferably + and −60 degree angles (Position A and Position B) with respect to the aligned fiber 111 collected between two wires (parallel collectors) 112 to create the angle-ply nanofiber structures depicted in FIG. 11. Another method is to collect the aligned fiber 111 between two wires 112 in a stand (not shown), capturing the aligned nanofiber membrane with nanofibers oriented at oblique angles, preferably + and −60 degree angles (Position A and Position B) to coat the NP disc 509 using the angle-ply fibrous structures created on the stand. The NP disc 509 can be mounted vertically for the second method. FIG. 10 shows the aligned electrospun nanofibers between two charged wires. Other methods to collect the aligned fibers 111 including alternative collector types such as charged parallel plates and charged rotating discs are anticipated. Creating aligned nanofibers to be intercepted and positioned at oblique angles in adjacent layers is the objective.

Referring to FIG. 11, multiple layers of fibrous structures 115 comprising angle-ply nanofibers 116 can be produced by the methods of the present invention (FIG. 3, 30), where the angle-ply nanofibers 116 in each layer are aligned cross-directionally to the nanofibers in adjacent layers. Collagen (CG) is the major insoluble fibrous protein in the natural extracellular matrix and in connective tissue. Research shows that collagen-coated biodegradable polymer nanofiber mesh has potential for both in vitro and in vivo cells growth. CG can be deposited on single or multilayers of angle-ply fibrous structures 115 by spraying CG solution. Multilayers of aligned PCL-CG can be deposited on NP disc by repeating deposition of PCL nanofiber and CG. The final AF structure 117 comprises repeating layers of aligned PCL nanofiber held together by CG to produce the final AF structure.

Figure 6:
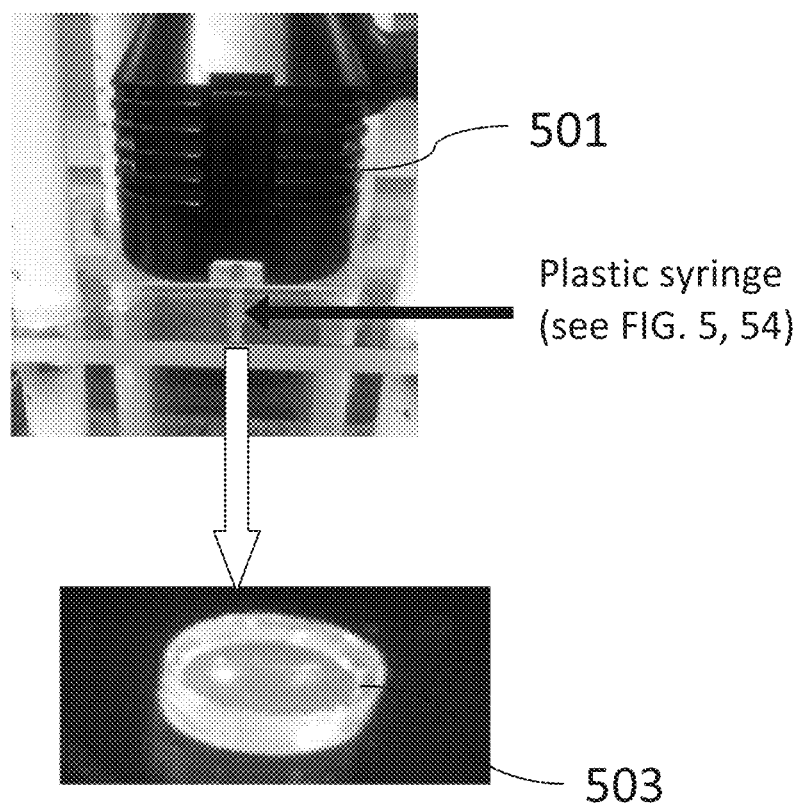
FIG. 6 is a non-limiting image showing (a) setup for curing of PEGDA solution in a plastic syringe at the UV chamber and (b) a produced PEGDA disc that was removed from the plastic syringe chamber.

The preferred method of the present invention (FIG. 3, 30) may be used to create multiple layers of angle-ply nanofiber structures 115 around the circumference of NP disc 509. Aligned PCL angle-ply nanofiber structures can be deposited on the NP disc 509 by rotating (manual or automated) the NP disc preferably at least 6 times (+ and −60 degrees) and dried in the UV chamber (FIG. 6, 501). After application of 6 layers of angle-ply nanofiber structure on the NP disc 509, the disc may be soaked with collagen solution. Collagen solution can be prepared by mixing 2.3 microliter of type I collagen with 0.23 microliter of acetic acid (2%) and 195 microliter of deionized water in a vortex mixer. The above application of CG and PCL nanofiber coating on NP may be repeated at least 3 times to produce an engineered IVD.

Figure 12:
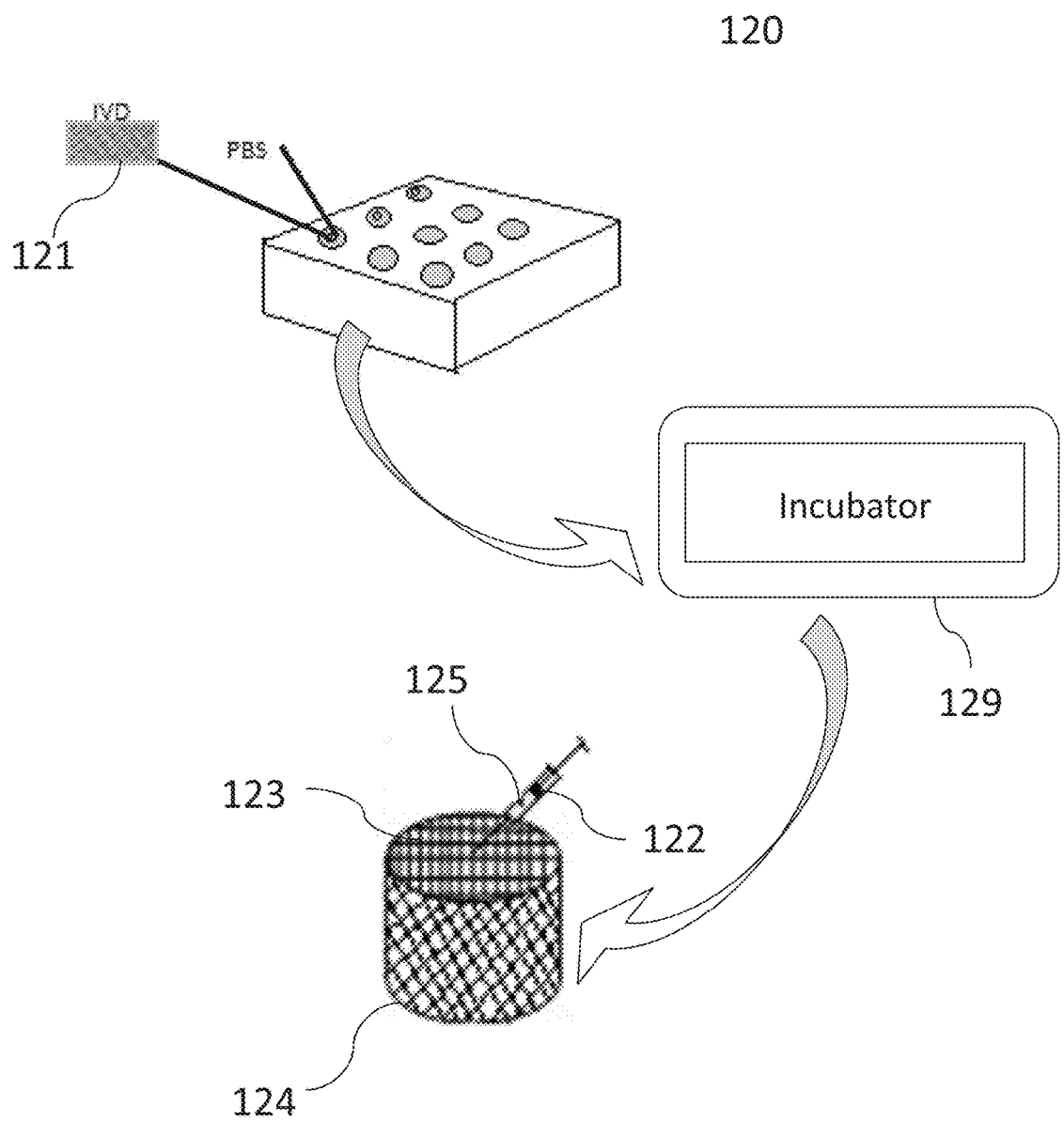
FIG. 12 is a non-limiting diagram showing one method of the present invention for preparation of PEGDA based tissue engineered IVD.

Referring now to FIG. 12, the process 120 is shown for performing (FIG. 3, 34) Step 4: Finalization of Engineered IVD.

Silicone Based IVD (Non-Tissue Engineered IVD) (FIG. 3, 341):

No further processing is required to fabricate a silicone based IVD for the implantation in the spine, where PCL electrospun nanofiber (ENF) anchors the silicone NP material on all sides in accordance with the methods provided by the process of the present invention as previously presented herein.

PEGDA Based Tissue Engineered IVD (FIG. 3, 342):

Polyethylene Glycol Diacrylate (PEGDA) tissue scaffolds having thickness higher than 1 mm have been shown to have limited applications as a three-dimensional cell culture devices due to the inability of cells to survive within the scaffolds. Without access to adequate nutrients, cells placed deep within the PEGDA tissue construct having thickness greater than 1 mm die out, leading to non-uniform tissue regeneration. Since PEGDA material has high degradation rate in comparison to PCL fiber materials, the PEGDA based IVD 121 can be soaked with Phosphate Buffered Saline (PBS) or Hanks' Balanced Salts (HBSS) solution for approximately two weeks at 38 degree centigrade in an incubator 129 to disintegrate the PEGDA. HBSS forms a solution that contains necessary minerals for bone cells to grow. PBS and HBSS are available from Sigma-Aldrich, LLC. When PEGDA material is fully disintegrated, any type of NP cell seeded hydrogel material 125 (such as sodium alginate, polyvinyl alcohol (PVA)-polyvinyl pyrrolidone (PVP)) can be injected 122 as illustrated in FIG. 12 into the IVD 123 while maintaining standard cell culture conditions. After an appropriate, well understood period of cell culture, the engineered IVD 123 illustrated in FIG. 12 can be ready for the implantation in the spine.

In developing the methods provided by the process of the present invention (FIG. 3, 30), the degradation of PEGDA was observed during laboratory testing within approximately two days after soaking the disclosed PEGDA IVD 121 in PBS in an incubator 129 (FIG. 12). Poly(vinyl alcohol) (PVA)/poly(vinyl pyrrolidone) (PVP) (PVA/PVP) hydrogel 125 may be injected 122 into the PEGDA hydrogel. The PVA/PVP hydrogel 125 injected 122 into the PEGDA hydrogel replaces the degraded PEGDA material. PVA/PVP hydrogel 125 may be prepared using a 95% to 5% by weight ratio of PVA and PVP, respectively. PVA and PVP powders (available from Sigma-Aldrich, LLC) may be dissolved in de-ionized water in an autoclave at 120° C. for approximately 1 hour. The solution may then be removed from the autoclave and homogenized by sonication in order to ensure removal of air bubbles. Once the sonication process is complete, the polymer should preferably undergo 6 freeze and thaw cycles in order to induce the cross-linking process.

PCL/PEGDA Composite Tissue Engineered IVD (FIG. 3, 343):

The methods provided by the process of the present invention as applied to produce a PEGDA based tissue engineered IVD (FIG. 3, 342) can be implemented for PCL nanofiber and PEGDA composite tissue engineered IVD (FIG. 3, 343) as illustrated in FIG. 7. Applying appropriate, well understood cell culture protocols, NP, AF and cartilage cells can be seeded as illustrated in FIG. 12 into the PCL nanofiber and PEGDA composite NP scaffold 123, the angle-ply structure and the end plates, respectively. After culmination of cell culture, the PCL nanofiber and PEGDA composite engineered IVD 124 illustrated in FIG. 12 can be implanted in the spine.

Measurement of Mechanical Performance of Silicone IVD
    Objectives:

Natural NP needs to withstand frequency sensitive viscoelastic behavior. Testing by the inventor determined the viscoelastic properties of a silicone IVD under static load and compared the values with natural NP to evaluate the feasibility of the gels as the potential implants.

Biomechanical Analysis:

A compression test setup was used to find the gel compressive modulus. The gel was compressed to 80% of the gel height at a rate 0.05 mm/sec during the unconfined compression tests. Viscosity and oscillation tests were performed on the hydrogel using the Malvern CVO-100 rheometer at 5%, 10%, and 15% strain rate at frequency 1 Hz. Viscous, elastic and complex modulus was found from the experiment.

Outcome:

Table 1 shows that the compressive modulus, complex shear modulus and phase shift angle of silicone gels and engineered IVD are in the range of human NP. These results confirm the suitability of electrospun nanofiber anchorage to gels, since it improves the mechanical properties of the gels. In addition, a wide range of viscoelastic silicone gels can be produced by changing the amount of cross-linker agents with base. The results indicate that silicone engineered IVD are bio-mechanically suitable as a replacement disc and feasibile in IVD applications.

| Experimental parameters | Human NP | Silicone gel | Silicone IVD |
| --- | --- | --- | --- |
| Compressive modulus (kPa) | $64.9 \pm 44.1^{33}$ | 38.75 | 87.47 |
| Complex modulus (kPa) | $7{\sim}20^{34}$ | $0.133 \pm 0.006$ | $26.54 \pm 7.54$ |
| Phase shift angle (degree) | $23{\sim}30^{34}$ | $27.52 \pm 0.83$ | $21.73 \pm 7.99$ |

Applications to Engineered Articular Cartilage (EAC)

The present invention (FIG. 3, 30) provides a process by which both non-tissue engineered and tissue engineered cartilaginous-like structures can be fabricated. The intervertebral disc (IVD) is a cartilaginous structure that resembles articular cartilage in its biochemistry, and shares a range of biomechanical properties. The mechanical role of the IVD is to resist and redistribute compressive normal and shear forces within the spine, and to withstand tension normal and shear forces. The IVD comprises discrete fibrous sheets with specialized collagen alignment that endure multi-directional loads.

Articular cartilage is a thin (2 mm to 4 mm) layer of specialized connective tissue, the principal function of which is to provide a smooth, lubricated surface for low friction joint articulation and transmission of loads to underlying subchondral bone. Articular cartilage has the ability to withstand high cyclic loads, and demonstrates little or no evidence of damage or degenerative change under such loads. Articular cartilage does not have blood vessels, nerves, or lymphatics, which is also characteristic of IVD. Articular cartilage is composed of a dense extracellular matrix (ECM) with a sparse distribution of highly specialized cells called chondrocytes. The ECM is principally composed of water, collagen, and proteoglycans, with other noncollagenous proteins and glycoproteins present in lesser amounts. Together, these components help to retain water within the ECM, which is critical to maintain its unique mechanical properties.

The biomechanical behavior of articular cartilage is biphasic: a fluid phase and a solid phase. Water is the principal component of the fluid phase, contributing up to 80% of the wet weight of the tissue. The solid phase is characterized by the ECM, which is porous and permeable. The initial and rapid application of articular contact forces during joint loading causes an immediate increase in interstitial fluid pressure. This local increase in pressure causes the fluid to flow out of the ECM, generating a large frictional drag on the matrix. When the compressive load is removed, interstitial fluid flows back into the tissue. The low permeability of articular cartilage prevents fluid from being quickly squeezed out of the matrix.

The methods provided by the processes of the present invention (FIG. 3, 30) in constructing an engineered IVD may be applied in fabricating engineered articular cartilage (EAC) that mimics the biomechanical behavior of natural articular cartilage. The ability provided by the methods of the present invention (FIG. 3, 30) to control alignment, spacing, and angular non-woven deposition of multiple layers of nanofibers combined with infusion of hydrogel is anticipated to enable structuring fiber-dense scaffolds that function much like collagen fiber ultrastructure and ECM in natural articular cartilage.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

We claim:

1. An engineered intervertebral disc (IVD) comprising:
   a solid compressible disc consisting of one of swelled or unswelled nucleus pulposus (NP) gel, said disc further comprising a first surface, a second surface, and a circumferential surface;
   at least one layer of nanofibers being one of aligned or randomly oriented and adjoining said first surface, said second surface, and overlapping on said circumferential surface;
   a nanofiber scaffold structure encompassing said at least one layer of nanofibers overlapping on said circumferential surface, said nanofiber scaffold structure consisting of multiple layers of nanofibers, said nanofibers in each layer being applied as single strips of aligned substantially parallel nanofibers arranged concentrically around said circumferential surface and directionally alternating relative to fibers in an adjacent layer, and
   wherein said nanofiber scaffold structure comprises an angle-ply mesh structure,
   wherein said engineered IVD mimics the architecture of natural IVD, and
   wherein nanofibers encompass all surfaces of said engineered IVD.

2. The engineered IVD of claim 1, wherein said engineered IVD is adapted to exhibit structural characteristics similar to native annulus fibrous (AF) and end plate (EP) in a natural IVD, substantially replicating at least biomechanical behavior of the annulus fibrous (AF).

3. The engineered IVD of claim 2, wherein said NP gel comprises one of silicone, PEGDA, or composite layers of PCL nanofiber and PEGDA.

4. The engineered IVD of claim 3, wherein said composite layers of PCL nanofiber and PEGDA comprise a three-dimensional NP scaffold.

5. The engineered IVD of claim 4, wherein at least one of natural NP, AF, and cartilage cells are seeded into said NP scaffold.

6. The engineered IVD of claim 1, further comprising a composite scaffold made with multiple layers of randomly oriented or aligned nanofibers and multiple layers of PEGDA hydrogel discs.

7. The engineered IVD of claim 1, further comprising NP cell hydrogel.

8. The engineered IVD of claim 7, wherein said NP cell hydrogel is seeded by cell injection.

9. The engineered IVD of claim 1, wherein said mesh structure is adapted to support osteoblast cell adhesion and proliferation.

10. The engineered IVD of claim 1, further comprising a non-tissue or a tissue engineered IVD.

11. An engineered intervertebral disc (IVD), comprising:
    nucleus pulposus (NP) gel in a solid compressible shape, said shape comprising a first surface, a second surface, and a circumferential surface;
    at least one layer of aligned or randomly oriented nanofibers adjoined to said first surface and said second surface and forming an end plate on each said surface, said end plates interconnected one to the other by nanofibers overlapping on to said circumferential surface;
    a nanofiber scaffold structure adjoining said circumferential surface, said nanofiber scaffold structure consisting of multiple layers of nanofibers, said nanofibers in each layer being applied as single strips of aligned substantially parallel nanofibers arranged concentrically around said circumferential surface and directionally alternating relative to fibers in an adjacent layer, wherein said NP gel comprises at least silicone,
wherein said single strips of aligned substantially parallel nanofibers are applied to said circumferential surface by intercepting electrospun nanofibers extended between opposing collectors comprising any one of charged wires, plates or rotating discs,
wherein said engineered IVD mimics the architecture of natural IVD, and
wherein nanofibers encompass all surfaces of said engineered IVD.

12. The engineered intervertebral disc (IVD) of claim 11, wherein said fibers in one layer of said nanofiber structure are angled at an oblique angle in the range of 40 to 80 degrees and preferably 60 degrees with respect to fibers in adjacent layers to mimic natural IVD annual fibrous (AF).

13. An engineered intervertebral disc (IVD), comprising:
multiple composite layers of nucleus pulposus (NP) gel and PCL nanofibers collectively forming a solid compressible shape, said shape comprising a first surface, a second surface, and a circumferential surface;
at least one layer of aligned or randomly oriented nanofibers adjoined to said first surface, said second surface, and overlapping on to said circumferential surface, and forming an end plate on each said first and second surface, said end plates interconnected one to the other by said nanofibers overlapping on to said circumferential surface;
a nanofiber scaffold structure encompassing said at least one layer of aligned or randomly oriented nanofiber overlapping on said circumferential surface, said nanofiber scaffold structure consisting of multiple layers of nanofibers, said nanofibers in each layer being applied as single strips of aligned substantially parallel nanofibers arranged concentrically around said circumferential surface and directionally alternating relative to fibers in an adjacent layer,
wherein said NP gel comprises one of PEGDA, or layers of composite of PCL nanofiber and PEGDA,
wherein said single strips of aligned substantially parallel nanofibers are applied to said circumferential surface by intercepting electrospun nanofibers extended between opposing collectors comprising any one of charged wires, plates or rotating discs,
wherein said engineered IVD mimics the architecture of natural IVD, and
wherein nanofibers encompass all surfaces of said engineered IVD.

14. The engineered IVD of claim 13, wherein said composite of PCL nanofiber and PEGDA layers form a three-dimensional NP scaffold.

15. The engineered IVD of claim 14, wherein said three-dimensional NP scaffold is stable absent PEGDA when said PEGDA is disintegrated.

16. The engineered IVD of claim 15, wherein any of natural NP, AF and cartilage cells are seeded into said NP scaffold absent PEGDA.

* * * * *